(12) United States Patent
Baumoel

(10) Patent No.: US 6,405,603 B1
(45) Date of Patent: Jun. 18, 2002

(54) METHOD FOR DETERMINING RELATIVE AMOUNTS OF CONSTITUENTS IN A MULTIPHASE FLOW

(76) Inventor: Joseph Baumoel, 104 Fairway View Dr., The Hamlet, Commack, NY (US) 11725

( * ) Notice: Subject to any disclaimer, the term of this patent is extended or adjusted under 35 U.S.C. 154(b) by 0 days.

(21) Appl. No.: 09/815,918

(22) Filed: Mar. 23, 2001

(51) Int. Cl.[7] ................................................. G01F 1/32
(52) U.S. Cl. ........................ 73/861.24; 73/592; 73/599
(58) Field of Search ........................ 73/861.24, 861.04, 73/861.25–861.29, 1.82, 61.45, 592, 599

(56) References Cited

U.S. PATENT DOCUMENTS

| | | |
|---|---|---|
| 4,397,190 A | 8/1983 | Hulin |
| 4,628,725 A | 12/1986 | Gouilloud et al. |
| 4,660,414 A | 4/1987 | Hatton et al. |
| 4,727,489 A | 2/1988 | Frazier et al. |
| 4,751,842 A | 6/1988 | Ekrann et al. |
| 4,862,060 A | 8/1989 | Scott et al. |
| 4,882,928 A | 11/1989 | Lane, Jr. et al. |
| 4,975,645 A | 12/1990 | Lucas |
| 5,101,164 A | 3/1992 | Marrelli |
| 5,117,698 A | 6/1992 | Baumoel |
| 5,251,488 A | 10/1993 | Haberman et al. |
| 5,259,239 A | 11/1993 | Gaisford |
| 5,260,667 A | 11/1993 | Garcia-Golding et al. |
| 5,353,627 A * | 10/1994 | Diatschenko et al. ...... 73/19.03 |
| 5,473,934 A | 12/1995 | Cobb |
| 5,524,475 A | 6/1996 | Kolpak et al. |
| 5,561,245 A | 10/1996 | Georgi et al. |
| 5,599,100 A | 2/1997 | Jackson et al. |
| 5,631,413 A | 5/1997 | Young et al. |
| 5,675,506 A | 10/1997 | Savic |
| 5,719,329 A | 2/1998 | Jepson et al. |
| 5,777,278 A | 7/1998 | Bednarczyk et al. |
| 5,929,342 A | 7/1999 | Thompson |
| 6,062,091 A * | 5/2000 | Baumoel .................. 73/861.27 |
| 6,332,361 B1 * | 12/2001 | Yamada et al. ................ 73/627 |

* cited by examiner

Primary Examiner—Benjamin R. Fueller
Assistant Examiner—Jewel Thompson
(74) Attorney, Agent, or Firm—F. Chau & Associates, LLP

(57) ABSTRACT

A method for determining constituent fluids for a multiphase flow in a pipe is provided by mounting two transducers on a pipewall. The first and second transducers are longitudinally offset in a longitudinal direction parallel to the flow. A first sonic wave is generated through the pipewall and is split into a pipewall wave and a transverse wave. The pipewall wave travels in the pipewall directly between the transducers, and the transverse wave is reflected through the flow between the transducers. With knowledge of one of the fluids in the flow, attenuation is measured of the transverse wave relative to the pipewall wave to determine proportions of constituent liquids in the flow. Amplitude fluctuations are determined in the transverse wave relative to the pipewall wave, and based on the amplitude fluctuations, proportions of gas bubbles in the flow are determined.

23 Claims, 4 Drawing Sheets

METHOD FOR DETERMINING RELATIVE AMOUNTS OF CONSTITUENTS IN A MULTIPHASE FLOW

BACKGROUND

1. Technical Field

This disclosure relates to sensing systems and more particularly, to a system for sensing relative amounts of constituents present in a multiphase liquid/gas mixture.

2. Description of the Related Art

It is recognized that multiphase liquid gas/mixtures occur naturally, as in the liquid, which emerges from wellheads at oil production fields. Such mixtures are, at the present time, separated so that the relative percentage of each may be determined. The result of this determination may be a change in the way a well is developed, or in the way that the products of such wells, in areas of mutual development, are managed, especially where use of common product pipe transmission may be desired.

Under such circumstances, it is highly desirable to measure not only the total flow rate of such a multiphase liquid, but also to accurately determine how much of each constituent may be present in the mixture delivered. As oil emerges from a well head, the oil frequently includes both gas and water. Water is usually injected from the surface to drive the oil to the well. It is important to know the percentage of oil, gas and water on a real time basis to assure that the well is operating efficiently, or if it is necessary to take action to improve its efficiency. However, it is difficult to measure such a multiphase liquid to determine the relative percentages flowing at a given time, or even over a given period of time.

In the production of oil, it is frequently found that natural gas resides in the same strata as the oil, which is being produced. When such wells are on land, it is economical to separate the gas from the oil, and then store, transport, treat and market the gas as well as the oil. However, when such a well is offshore, the storage space for the gas is usually not available, and it would be necessary to install an expensive pipeline from the offshore well to a land based storage facility.

In addition, when the pressure of the well is low, it is necessary to pump water, or other chemicals down to the well to force the oil to the surface. Accordingly, what comes up is frequently a mixture of oil, gas and water, in variable proportions. To judge the performance of the well, it is necessary to know these proportions, and thus enable the operators to "treat" the well to enhance its performance. For this and other reasons, such as evaluating the relative performance of different wells, it is desired to measure the flow rate of the multiphase gas/liquid, and determine the proportions of each component.

At present there are such instruments to measure multiphase flows. In general, they operate by a combination of means, such as various types of flow meters, such as turbine, capacitive correlation flow meters and dielectric constant sensors, various conventional mechanical flow meters, and radioactive density sensing devices. Unfortunately, such instruments are extremely expensive, ranging in price from about $200,000 to several million, not including the expense of installation at the wellhead.

Therefore, a need exists for an apparatus to perform the measurement of amounts of multiphase fluids in a multiphase flow. A further need exists for providing an easily and economically implemented way of providing multiphase flow measurements, which does not disrupt the flow of the multiphase fluid.

SUMMARY OF THE INVENTION

A non-intrusive flowmeter for measurement of a multiphase liquid in a pipeline is disclosed. The present invention may operate as both a flowmeter and as a means of determining the relative quantity of constituent materials in a flow, for example, Oil, Water and Gas flowing in a pipe. The present invention employs the ability of a Wide Beam Clamp-On Ultrasonic flowmeter to operate at high levels of aeration and non-homogeneity of the flow. In addition, this type of flowmeter is capable of analyzing the received sonic data to identify the relative amount of constituents, e.g., gas and water in oil, by the effect that these components have on the sonic properties of the medium, and by the effect on the received signal amplitude.

A method for determining constituent fluids for a multiphase flow in a pipe is provided by mounting two transducers on a pipewall. The first and second transducers are longitudinally offset in a longitudinal direction parallel to the flow. A first sonic wave is generated through the pipewall and is split into a pipewall wave and a transverse wave. The pipewall wave travels in the pipewall directly between the transducers, and the transverse wave is reflected through the flow between the transducers. With knowledge of one of the fluids in the flow, attenuation is measured of the transverse wave relative to the pipewall wave to determine proportions of constituent liquids in the flow. Amplitude fluctuations are determined in the transverse wave relative to the pipewall wave, and based on the amplitude fluctuations, proportions of gas bubbles in the flow are determined.

These and other objects, features and advantages of the present invention will be come apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

The present invention includes an apparatus for measuring amounts of constituent materials in a multiphase flow. The present invention is applicable in many industries, for example, oil production, chemical plants, etc. where multiphase flow in a pipe is encountered. The present invention provides a system and method for determining constituent ratios of multiphase fluid flows by employing a sonic-based flow meter. The present invention also provides volume fraction information about the constituent materials when flow rate information is available.

Figure 1:
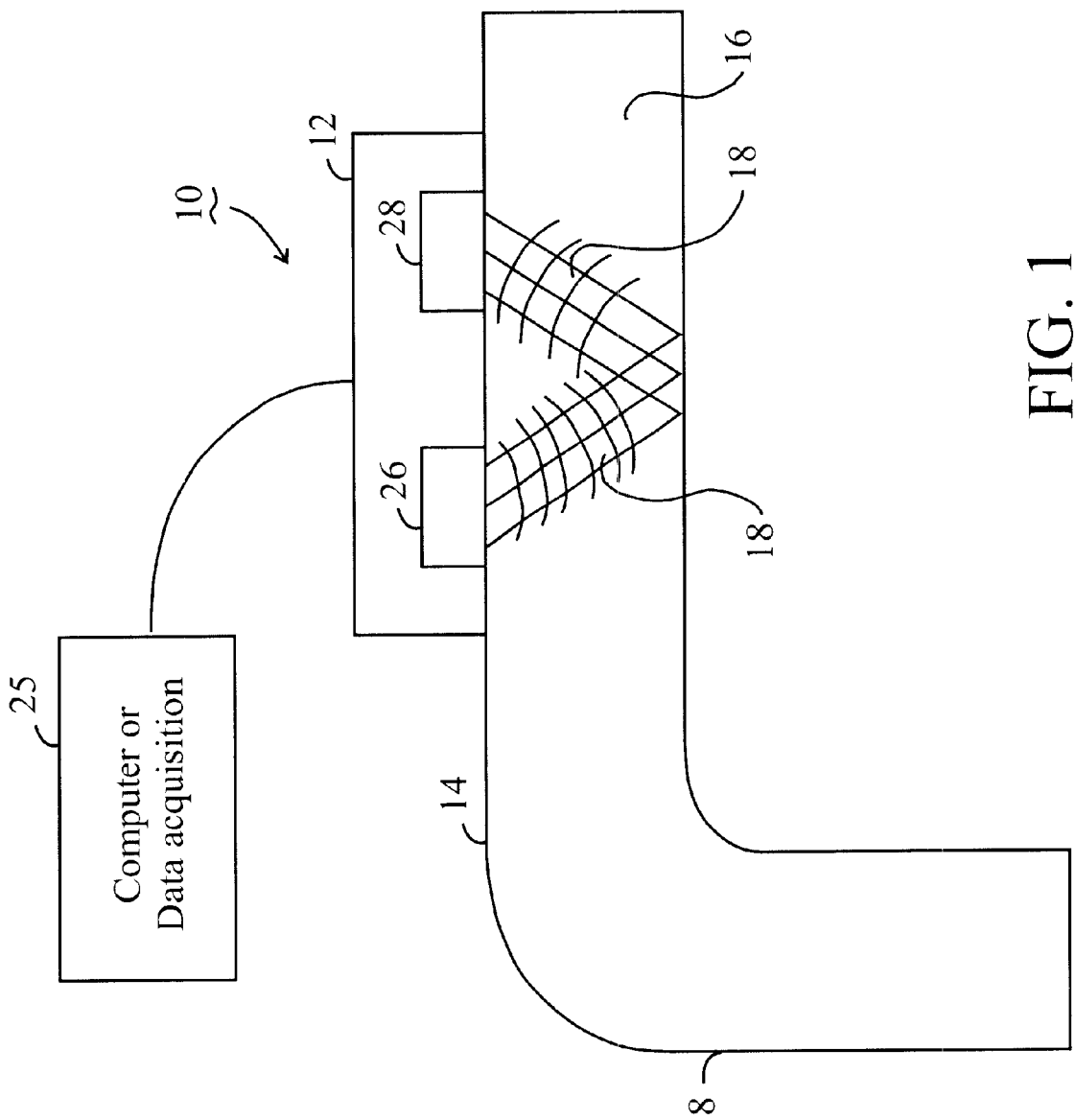
FIG. 1 is a cross-sectional view of a pipe system having a flow meter system employing the present invention.

Referring now in specific detail to the drawings in which like reference numerals identify similar or identical elements throughout the several views, and initially to FIG. 1, a system 10 is shown in accordance with one embodiment of the present invention. System 10 includes a wide beam transit-time ultrasonic flow meter 12, as described in U.S. Pat. No. 5,117,698, incorporated herein by reference. Flow meter 12 preferably is a clamp-on type, which clamps to an exterior wall of a pipe, duct or channel 14 to permit flow to be measured therein. Flow meter 12 is modified in accordance with the present invention to provide multiphase flow measurements and to determine relative proportions of constituents of a flow 16 in pipe 14.

The clamp-on wide beam transit-time ultrasonic flow meter 12 includes a set of ultrasonic transceivers (transducers 26 and 28), which are clamped to the exterior of pipe 14 so as to inject sonic energy into pipe 14. Flow meter 12 permits the sensing flow of a homogeneous liquid in a pipe. However, in accordance with the present invention, the wide sonic beam principle, which is based on the injection of sonic energy into the pipe wall may be employed to determine constituent fluids (i.e., gases and liquids) in the flow. The sonic energy in the form of a wide beam 18 is injected in pipe 14 in a way which excites a natural mode of sonic transmission of the pipe. In this way, sonic waves travel down pipe 14 and are measured by transducer 28. A computer or data acquisition device 25 may be employed with flow meter 12 to perform computations to determine flow rates, proportions of the constituents material of flow 16, storing lookup tables or other parameters needed to determine characteristics of flow 16.

Figure 2:
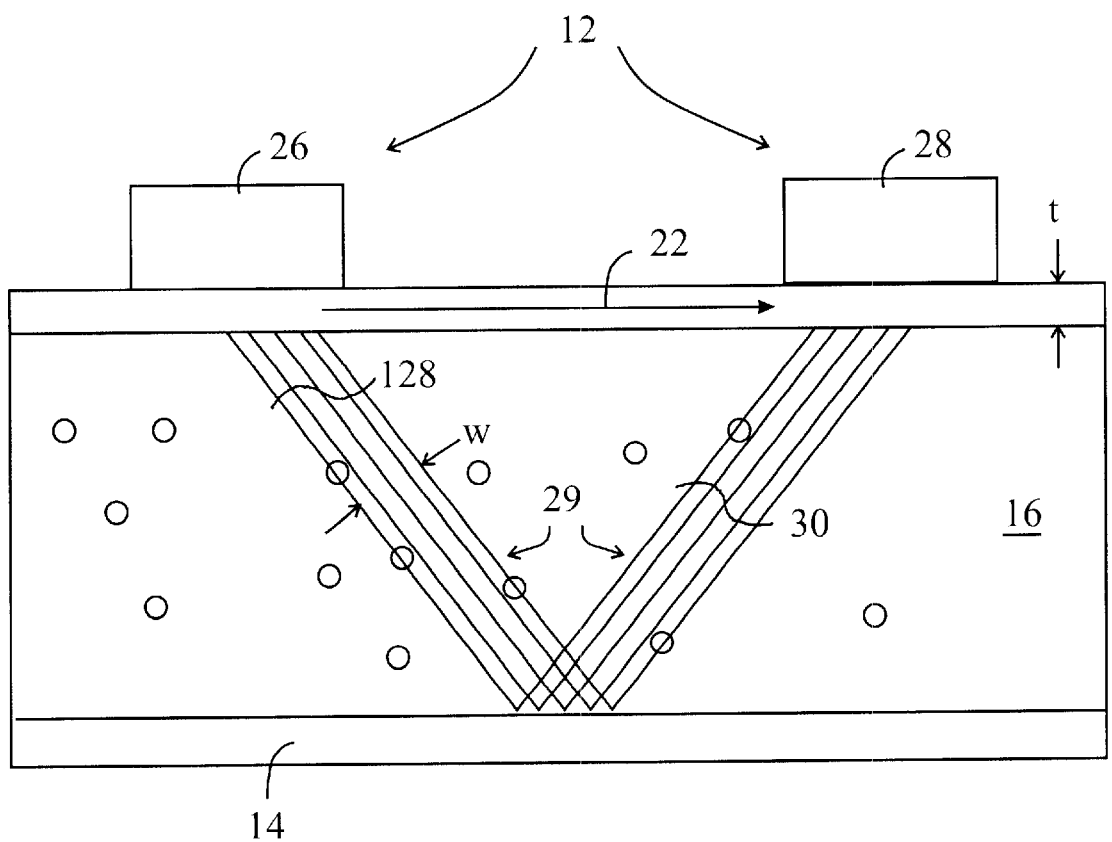
FIG. 2 is a cross-sectional view of the pipe system of FIG. 1 showing greater detail of sonic energy waves in accordance with the present invention.

Referring to FIG. 2, a schematic diagram is shown to demonstrate the operation of the present invention. A natural mode of sonic energy transmission is excited in pipe 14, in which a transverse wave 22 travels axially down the pipe wall at the velocity characteristic of the pipe's material, and at a frequency dependent on the pipe material and a wall thickness "t". To generate such a wave, a transducer 26 of flow meter 12 operates at this preferred frequency (f), and has a phase velocity ($v_{phase}$) that matches the speed that the axially directed wave 22 travels down the pipe.

When such a wave 22 is generated, as it travels down the pipe wall, wave 22 radiates a sonic wave 128 into the liquid/gas flow, which ultimately reflects off the far wall and reenters the pipe wall on the same side of the pipe from which is was originally transmitted, as wave 30. As wave 30 travels down the pipe wall to the place where a transducer 28, like transducer 26 is located. The sonic energy then enters this "receive" transducer 28 and generates a receive signal.

This receive signal is influenced by the flow through which reflected wave 29 has passed. The arrival time of the wave 29 is influenced by the natural sonic propagation velocity of the fluid, and to a small degree by flow, and the amplitude of the wave 29 is affected by the degree of attenuation imposed by the liquid on wave 128. This attenuation is caused by both the effect of the viscosity of the liquid, which takes energy from the sonic beam, and the scattering effect of any particulate or differentiated material included in the liquid.

In an example for oil production, a multiphase flow 16 includes oil, water and gas (e.g., natural gas). Since the sonic propagation velocity of water is well known, the effect of its presence in a mixed liquid can be determined in relation to the proportion of two liquids in the flow.

The sonic propagation velocity of the flow (liquid) is preferably and accurately measured by the wide beam transit-time ultrasonic flow meter, as described in U.S. Pat. No. 5,117,698. In accordance with the present invention, this measurement may be scaled to determine the percentage of water in a particular type of oil. It should be noted, that the presence of water, if not emulsified, will act to some degree as a sonic beam scattering mechanism. This scattering effect can be quantified and classified to reduce its impact on the multiflow constituent measurement. With knowledge of one liquid in the flow, a second liquid's proportions can be determined. Advantageously, by measuring the difference in sonic velocity between beam or wave 22 and wave 29 a determination of density can be determined for the fluids in the pipe. It should be noted that pipe 14 acts as a beam splitter, splitting the sonic beam between the pipe wall (beam 22) and through the fluid (beam 128).

The presence of undissolved gas in the liquid stream also serves to scatter the sonic energy, so that the sonic energy or wave 29 does not arrive at the receive transducer, or if it does, arrives at a different time. Since the sonic beam produced by the wide beam transducer 26 is wide (W), and the size of the gas bubbles, for all but the highest possible percentages of gas, is smaller than the width of the sonic beam, the effect of the gas is not to totally interrupt the beam, but rather to cause its amplitude to fluctuate.

Flow meter 12 also measures the sonic amplitude by its effect on a signal amplitude regulation mechanism parameter. This flow meter 12 is capable of determining the amount of free gas by the degree of variability of this parameter. In other words, by monitoring the fluctuations in amplitude of the measured beams (waves 22 and 29) the amount of free gas can be determined in the flow.

Figure 3:
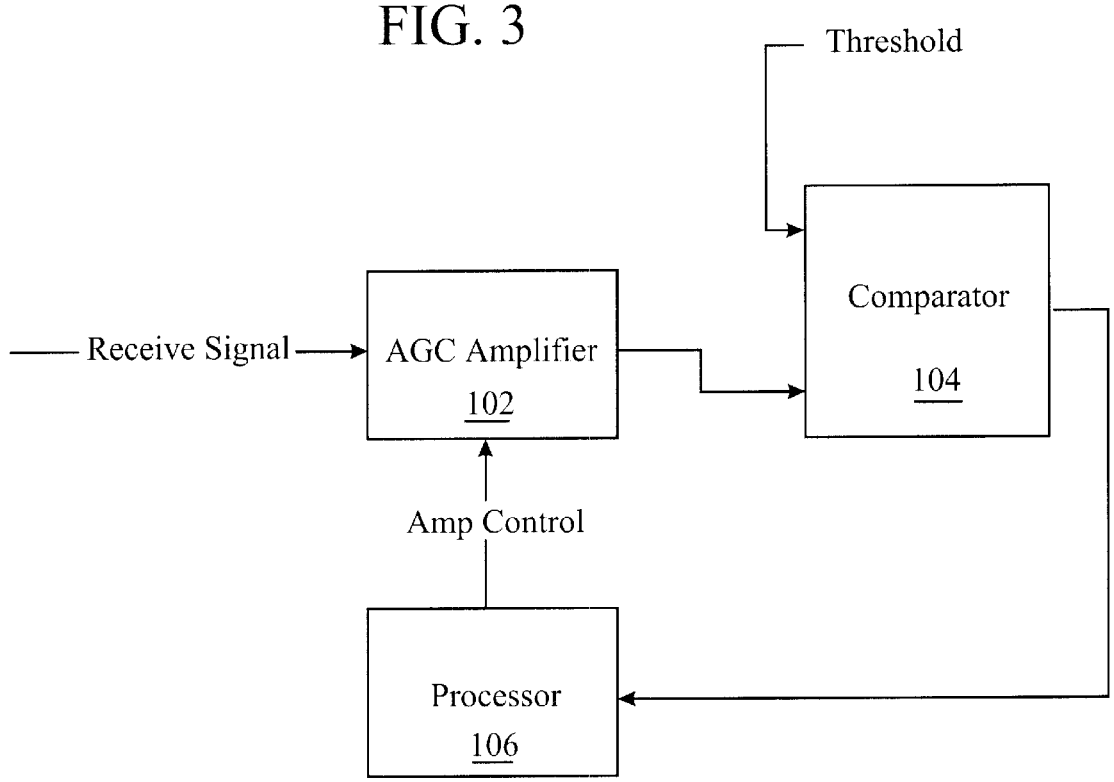
FIG. 3 is a schematic diagram of an automatic gain control circuit which may be employed to determine gas bubbles in a flow in accordance with the present invention.

Referring to FIG. 3, in one embodiment, transducers 26 and 28 include automatic gain control (AGC) amplifiers 102, which are employed to maintain a constant amplitude for signals output from flow meter 12. A received signal is received in amplifier 102 and amplified a predetermined amount. The amplified signal is compared to threshold value in a comparator 104. The threshold value is employed to maintain the scaling of the amplified signal. The output of comparator 104 is input to a processor 106 which provides feedback to amplifier 102 to adjust the amplification of the signal input to amplifier 102. During amplitude fluctuations due to the presence of gas bubbles, the AGC amplifier 102 needs to work harder to maintain the constant gain level. The harder the ACG amplifier 102 works the more gas bubbles are present. Therefore, the AGC action is proportional to the amount of gas in the flow. Non-homogeneous flows such as flows with gas bubbles present can be determined. In one example, during normal operation without gas bubbles, an amp control signal, which is preferably a digital signal, fluctuates between digital ones and zeros. When gas bubbles are present, to maintain amplitude scaling the amp control signal will provide longer series of all ones (or zeros). These longer series can be employed as a measure of the gas in the flow. Other signals or methods may also be employed in accordance with the present invention.

Since, in the example, the presence of water in oil affects the measured sonic propagation velocity of the liquid, and to some degree the signal amplitude, and the presence of free gas affects the signal amplitude, but even the small degree of the gases ability to be absorbed into the liquid under high pipeline pressure, does not affect the sonic propagation velocity in a measured way. In this way, the constituent amounts of oil, water and gas can be determined by measuring the sonic propagation velocity of the liquid, and the amplitude fluctuations of the amplitude of the received wave through the flow and the received wave directly from the pipe wall. The degree to which the liquid attenuates the sonic signal, and the variability of this signal which results from a non-homogeneous condition, such as produced by bubbles of free gas in the liquid phase, may advantageously be determined.

However, to determine the meaning of the signal attenuation produced by liquid conditions, a reference is needed that is independent from the liquid condition, and independent from the condition of the flow meter, whose transmitted sonic signal amplitude is variable with time, temperature, and the stability of the coupling of sonic energy from the transducer to the pipe.

Referring again to FIG. 2, transducer 26 produces a reference signal (wave 22). Note that the liquid's sonic signal of wave 29 is derived from the sonic signal that travels down the pipe wall (wave 22) from transducer 26. Wave 29 transmits the sonic energy to transducer 28, which also receives wave 22. Transducer 28 receives both the liquid signal (wave 29), and the signal that generated the liquid signal (wave 22). Pipe wall signal or wave 22 travels a shorter distance than the liquid wave 29, and travels at a higher velocity than the liquid wave 29, since the sonic velocity of solid pipe walls is higher than any sonic velocity in liquid. Therefore, wave 22 can be detected individually, separate from the detection of the liquid wave or signal 29.

Advantageously, wave 22 and wave 29 are affected equally by any change in transmission amplitude, by a change in coupling of the transducer, by a change in the gain of the flow meter signal amplifier that could affect the gain stabilization parameter that measures the sonic signal amplitude, etc. Therefore, the ratio of the measured amplitude of the liquid wave 29 to the wave 22 in the pipe wall is a stable measure of the effect of the liquid conditions in the flow on the amplitude of the liquid wave 29.

Thus, flow meter 12 has the ability, using this ratiometric amplitude measurement principle (see FIG. 3), the ability to measure the sonic propagation velocity of the liquid accurately, and to measure the flow rate accurately, (as described in U.S. Pat. No. 5,117,698) to provide parametric information related to the percentage of oil, water and gas in the multiphase flow in accordance with the present invention. It is to be understood that the reference to the water, oil, and gas multiphase flow is for illustrative purposes only. Other constituents may be present and measured in addition to or instead of these materials in accordance with the present invention.

The receiving transducer 28 gathers the liquid sonic propagation velocity, the signal amplitude, and the variability of the signal amplitude and uses this information to quantify characteristics of the flow. The quantities derived are employed to interpret the meaning and the proportions of the flow.

The output signals from transducers 26 and 28 may be employed in lookup tables to determine one or more of the density of the flow, the proportions of the constituent materials in the flow, the flow rate, etc. These quantities may be output from the flow meter directly, for example, to a display on the flow meter or input to a computer or other data acquisition device. Lookup tables are generated or populated, a priori, depending on the materials, which will be measured in the flow, pipe conditions and sizes or any other parameters, which may affect measurements.

Lookup tables may be generated by creating a matrix of known conditions versus measured flow meter signals. This may be performed by introducing measured quantities of water and gas into samples of either the same or representative oil, to determine the effect of the various percentages on the measurement parameters, and their ratios. For example, a pipe may be filled with 10% free gas, 40% oil and 50% water, and liquid sonic propagation velocity, signal amplitude, and variability of the signal amplitude may be measured and recorded in the lookup table. When signal values or characteristics are measured, they are compared to the signal values of the lookup table to determine the proportions of water, oil and gas. Tabulating these results into lookup tables will permit subsequent actual conditions to be read-out to inform operators of current conditions, e.g., in a well or its feedpipe 8 (FIG. 1).

The sonic wave 22 along pipewall may advantageously be used as a reference for zero flow conditions. Ordinarily, it is necessary to shut down flow to set the controls of any flow meter that can actually operate at zero flow, so that the meter's intrinsic offsets are determined and overcome. However, the pipe signal (wave 22) is the source of the liquid signal and is identical in every way, except that its upstream and downstream arrival time is not influenced by flow. Therefore, it is available to determine if there is any such offset, and if there is its direction and magnitude. With this information, it is possible to set the zero adjust of this flow meter automatically, e.g., automatically zero the flow meter, even if it is not possible to shut down flow. In fact, it is possible to automatically invoke an AutoZero function periodically to ensure against any source of zero drift, e.g., intermittent automatic zeroing. This function can be introduced into the flow meters.

Figure 4:
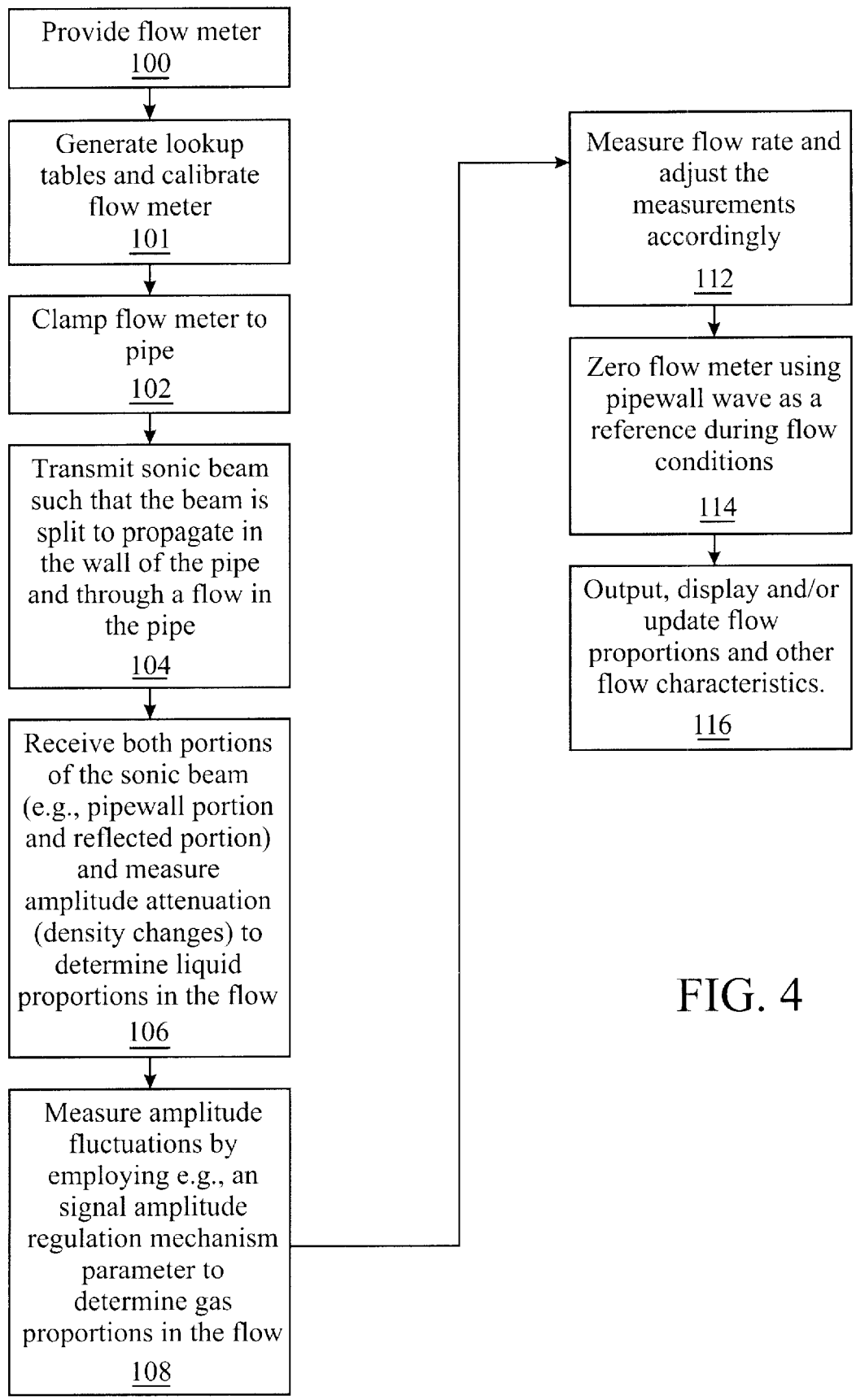
FIG. 4 is a block/flow diagram for a system/method for employing the present invention.

Referring to FIG. 4, a block/flow diagram for a system/method of the present invention is shown. In block 100, a flow meter is provided with transducers having the capability for measuring sonic velocity (e.g., liquid sonic propagation velocity and pipewall sonic velocity), signal amplitude, and the variability of the signal amplitude are provided. The transducers of the flow meter are calibrated in flows having various ratios of constituent materials. These calibrations result in the formulation of lookup tables, which correlate flow conditions versus transducer readings, in block 101.

In block 102, the flow meter preferably includes a clamp-on type and the flow meter is clamped to a pipe. One transducer of the flow meter is mounted upstream and one is mounted downstream. In block 104, one transducer transmits sonic signals into a multiphase flow (e.g., a flow including two liquids, a liquid and a gas, a gas and two liquids, etc.). The sonic signals propagate down the pipewall and into the flow to be attenuated and reflected back to the pipewall of the same side of the transmitting transducer. In block 106, the downstream transducer receives the sonic energy in the form of a direct pipewall wave and a reflected wave, and measures attenuation of the reflected signal using the signal directly propagated pipewall signal as a reference. The attenuated amplitude indicates densities of the liquids and therefore sonic velocities through the liquid. The sonic velocity information is employed to determine the constituent liquids in the flow.

In block 108, the fluctuations in amplitude of the attenuated signal are determined by comparing the reflected signal and the directly propagated pipewall signal (See e.g., FIG. 3). The amplitude fluctuations are employed to measure gas bubbles in the flow.

Flow rates are measured by the transducers in block 112. The flow rate measurements through the flow are employed to adjust the velocity measurements of the sonic energy waves to obtain more accurate results.

In block 112, the sonic readings obtained by the flow meter are correlated to the materials in the flow by employing the lookup tables to determine proportions of the materials in the multiphase flow. This comparison may be performed on the flow meter, if the flow meter includes a memory with lookup tables stored therein. Alternately, the signal information may be transmitted to a remote computer, a portable electronic device, such as a portable computer or data acquisition system to perform the correlation and display the results.

In block 114, the flow meter may be zeroed during flow or no-flow conditions by employing the pipe wall wave 22 as a reference against measurement offsets through the flow.

In block 116, proportions of constituent materials are output and updated in real time. Data collected from flow meters may be displayed on a display device, such as a computer monitor in a plurality of different formats to provide a user or monitor to easily determine flow constituents, flow rates or any other measurable parameters.

Advantageously, the display permits a volume fraction computation for the constituent materials present in the flow. This permits users to see the flow in real-time. For example, seeing a change in behavior of the distribution would soon be associated with various classes of wellhead problems, advantageously, permitting remedial action to be taken in a timely manner.

The volume fraction of constituent materials, in combination with the flow rate, as described above, permits publication of the expected volumes of each product component at an output of an ultimate separator. A variety of other diagnostic and flow related data is also contemplated.

The implementation of the determination of the volume fractions of multiphase constituent materials, for example, oil, gas and water, which is measured in real time by the present invention is described. The system utilizes the structure as described above to produce a visual display representing the continuously changing distribution of multiphase fluids as the fluids flow in a pipe.

It is desirable to provide real time interpretation of this data. For example, integration over a period of time of the total value of oil, gas and water that emerges from a wellhead is of interest. This is valuable in determining the current condition of the well, to indicate the need for corrective action to increase the efficiency of the well. It is also of value in determining the allocation of product among various suppliers who may be using a common pipeline for transportation of liquids emerging from different wells.

In particular, it is possible to eliminate the separation of oil, gas and water at the wellsite itself, which is often quite difficult and expensive.

In addition, the imaging of the distribution of oil, gas and water on a continuous basis provides operators with a real time understanding of the condition of each well. Changes that take place over time, or on occasion that occur suddenly, will be immediately observable relative to prior conditions. It is likely that certain conditions will be identifiable by a characteristic image.

Although the present invention has been illustratively described in terms of a three constituent flow. Other multiphase flows may be tested in accordance with the invention. The present invention is applicable to any multiphase flow for a variety of different industries.

Having described preferred embodiments for a novel sensing system for multiphase flow (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for determining constituent fluids for flow in a pipe, comprising the steps of:

providing a first sonic transducer and a second transducer on a pipewall, the first and second transducers being longitudinally offset in a longitudinal direction parallel to the flow;

generating a first sonic wave through the pipewall, the first sonic wave being split into a pipewall wave and a transverse wave, the pipewall wave traveling in the pipewall directly between the first and second transducers, the transverse wave being reflected through the flow between the first and second transducers; and measuring attenuation of the transverse wave relative to the pipewall wave to determine proportions of the constituent fluids in the flow.

2. The method as recited in claim 1, wherein the step of measuring attenuation includes measuring a velocity phase shift between the transverse wave and the pipewall wave.

3. The method as recited in claim 1, wherein the step of measuring attenuation further includes the steps of:

quantifying the attenuation; and comparing a quantified attenuation to a lookup table to determine the proportions of the constituent fluids in the flow.

4. The method as recited in claim 1, further comprising the step of measuring a flow rate of the flow and adjusting the sonic wave velocities in accordance with the flow rate.

5. The method as recited in claim 1, further comprising the step of zeroing the transducers by employing the pipewall wave to determine measurement offsets during flow conditions.

6. The method as recited in claim 1, further comprising the step of graphically displaying proportions of constituent materials on a display.

7. A method for determining constituent fluids for flow in a pipe, comprising the steps of:

mounting a first sonic transducer and a second transducer on a pipewall, the first and second transducers being longitudinally offset in a longitudinal direction parallel to the flow;

generating a first sonic wave through the pipewall, the first sonic wave being split into a pipewall wave and a transverse wave, the pipewall wave traveling in the pipewall directly between the first and second transducers, the transverse wave being reflected through the flow between the first and second transducers, the transverse wave including a width transverse to a direction of propagation of the transverse wave;

determining amplitude fluctuations in the transverse wave relative to the pipewall wave; and based on the amplitude fluctuations, determining proportions of gas bubbles in the flow, the gas bubbles having a size of less than the width.

8. The method as recited in claim 7, further comprising the step of:

with knowledge one liquid in the flow, measuring velocity attenuation of the transverse wave relative to the pipewall wave to determine proportions of the constituent fluids in the flow.

9. The method as recited in claim 8, wherein the step of measuring attenuation further includes the steps of:
quantifying the attenuation; and
comparing a quantified attenuation to a lookup table to determine the proportions of the constituent fluids in the flow.

10. The method as recited in claim 7, further comprising the step of measuring a flow rate of the flow and adjusting the sonic wave velocities in accordance with the flow rate.

11. The method as recited in claim 7, further comprising the step of zeroing the transducers by employing the pipewall wave to determine measurement offsets during flow conditions.

12. The method as recited in claim 7, wherein the step of determining amplitude fluctuations includes monitoring a signal amplitude regulation parameter to determine an amount of free gas by a degree of variability of the parameter.

13. The method as recited in claim 12, wherein the signal amplitude regulation parameter includes an automatic gain control amplifier.

14. The method as recited in claim 7, wherein the step of determining proportions of gas bubbles in the flow further includes the steps of:
quantifying the amplitude fluctuations; and
comparing quantified amplitude fluctuations to a lookup table to determine the proportions of free gas in the flow.

15. The method as recited in claim 7, further comprising the step of graphically displaying proportions of constituent materials on a display.

16. A method for determining constituent fluids for a multiphase flow in a pipe, comprising the steps of:
mounting a first sonic transducer and a second transducer on a pipewall, the first and second transducers being longitudinally offset in a longitudinal direction parallel to the flow;
generating a first sonic wave through the pipewall, the first sonic wave being split into a pipewall wave and a transverse wave, the pipewall wave traveling in the pipewall directly between the first and second transducers, the transverse wave being reflected through the flow between the first and second transducers, the transverse wave including a first width transverse to a direction of propagation of the transverse wave;
with knowledge on at least one of the fluids in the flow, measuring attenuation of the transverse wave relative to the pipewall wave to determine proportions of constituent liquids in the flow;
determining amplitude fluctuations in the transverse wave relative to the pipewall wave; and
based on the amplitude fluctuations, determining proportions of gas bubbles in the flow, the gas bubbles having a size of less than the first width.

17. The method as recited in claim 16, wherein the step of measuring attenuation further includes the steps of:
quantifying the attenuation; and
comparing a quantified attenuation to a lookup table to determine the proportions of the constituent fluids in the flow.

18. The method as recited in claim 16, further comprising the step of measuring a flow rate of the flow and adjusting the sonic wave velocities in accordance with the flow rate.

19. The method as recited in claim 16, further comprising the step of zeroing the transducers by employing the pipewall wave to determine measurement offsets during flow conditions.

20. The method as recited in claim 16, wherein the step of determining amplitude fluctuations includes monitoring a signal amplitude regulation parameter to determine an amount of free gas by a degree of variability of the parameter.

21. The method as recited in claim 20, wherein the signal amplitude regulation parameter includes an automatic gain control amplifier.

22. The method as recited in claim 16, wherein the step of determining proportions of gas bubbles in the flow further includes the steps of:
quantifying the amplitude fluctuations; and
comparing quantified amplitude fluctuations to a lookup table to determine the proportions of free gas in the flow.

23. The method as recited in claim 16, further comprising the step of graphically displaying proportions of constituent materials on a display.

* * * * *